(12) United States Patent
Sh. Revishvili et al.

(10) Patent No.: US 6,449,506 B1
(45) Date of Patent: Sep. 10, 2002

(54) MULTIPHASE DEFIBRILLATOR WITH CONDUCTIVE HOUSING

(75) Inventors: Amiran Sh. Revishvili, Moskau (RU); Tran Thong, Portland, OR (US)

(73) Assignee: Biontronik Mess-und Therapiegeraete GmbH & Co. Ingenieubuero Berlin, Berlin (DE)

(*) Notice: Subject to any disclaimer, the term of this patent is extended or adjusted under 35 U.S.C. 154(b) by 0 days.

(21) Appl. No.: 09/603,412

(22) Filed: Jun. 26, 2000

(30) Foreign Application Priority Data

Jun. 25, 1999  (DE) ......................... 199 30 267

(51) Int. Cl.⁷ ................................. A61N 1/39
(52) U.S. Cl. ............................................. 607/5
(58) Field of Search ..................... 607/4–5, 7

(56) References Cited

U.S. PATENT DOCUMENTS

| 4,708,145 A | * | 11/1987 | Tacker et al. ............... 607/5 |
| 4,727,877 A | * | 3/1988 | Kallok ........................ 607/5 |
| 5,224,476 A | | 7/1993 | Ideker et al. ............ 128/419 |
| 5,376,103 A | * | 12/1994 | Anderson et al. ........... 607/5 |
| 5,468,254 A | * | 11/1995 | Hahn et al. ................ 607/5 |
| 5,531,764 A | * | 7/1996 | Adams et al. ............... 607/5 |
| 5,601,607 A | | 2/1997 | Adams ....................... 607/5 |
| 5,690,686 A | * | 11/1997 | Min et al. .................. 607/5 |
| 5,865,838 A | | 2/1999 | Obel et al. ................. 607/5 |
| 5,916,238 A | * | 6/1999 | Hauser et al. ............. 607/5 |
| 6,233,483 B1 | * | 5/2001 | Causey et al. ............. 607/5 |

FOREIGN PATENT DOCUMENTS

| DE | 43 10 412 | 7/1994 |
| DE | 693 09 931 | 10/1997 |
| EP | 0 588 127 | 3/1994 |
| EP | 0 652 789 | 5/1995 |

OTHER PUBLICATIONS

B. Ken Knight, et al., "Dual Shock Defibrillation With a New Lead Configuration Involving and Electrode in the Left Posterior Coronary Vein", PACE, vol. 21, Apr. 1998, p. 806.

* cited by examiner

*Primary Examiner*—Kennedy Schaetzle
*Assistant Examiner*—Kristen Droesch
(74) *Attorney, Agent, or Firm*—Christie, Parker & Hale, LLP

(57) ABSTRACT

A defibrillator comprising an implantable housing (10) and an implantable electrode set which includes at least a right-ventricular electrode (2) and a coronary sinus electrode (3), wherein arranged in the housing (10) is a control device (11) for the electrodes of the electrode set wherein the housing (10) is conducting and is connected as an electrode.

8 Claims, 3 Drawing Sheets

MULTIPHASE DEFIBRILLATOR WITH CONDUCTIVE HOUSING

Figure 1:
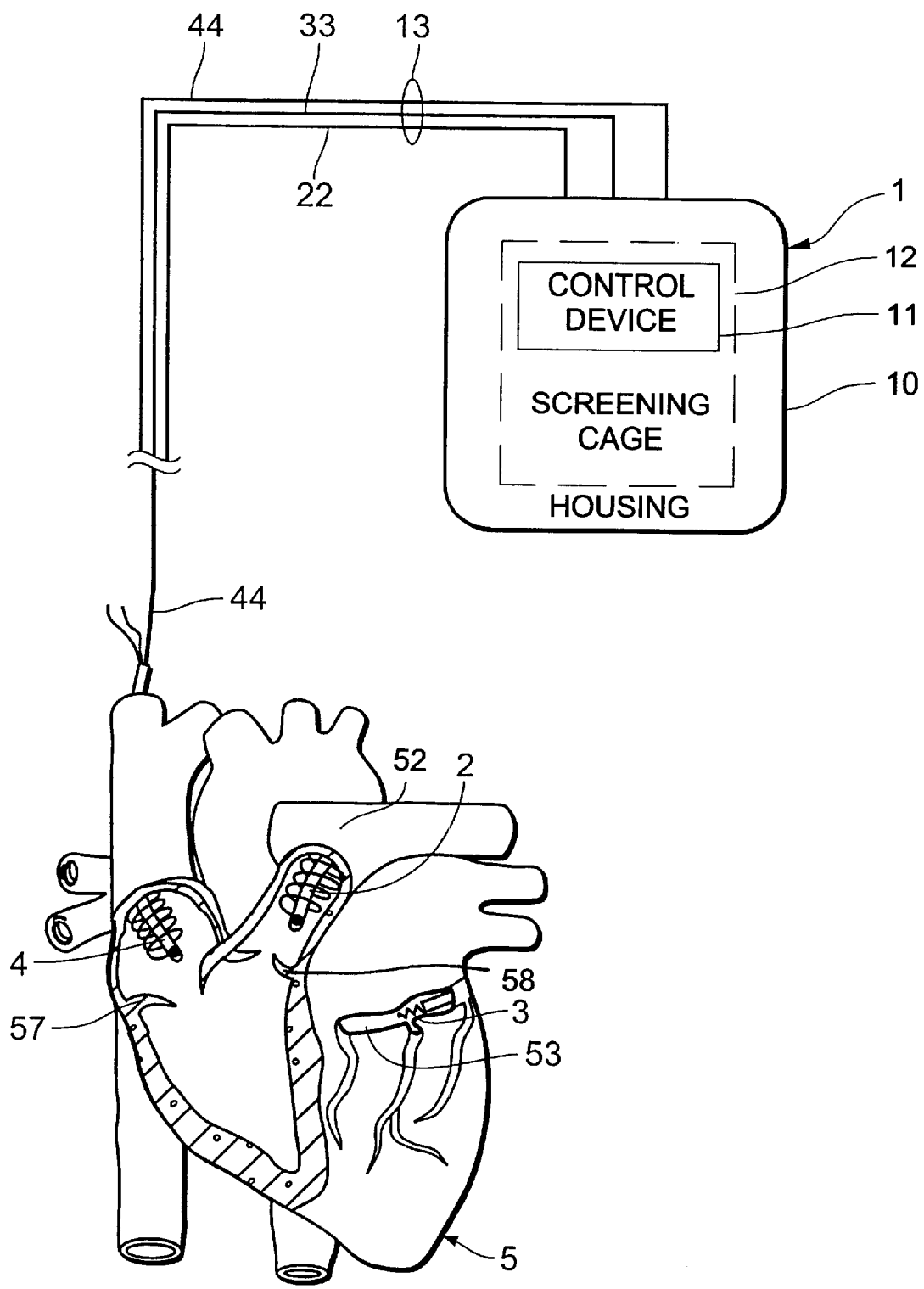

The invention concerns a defibrillator comprising an implantable housing and an implantable electrode set which includes at least a right-ventricular electrode and a coronary sinus electrode, wherein arranged in the housing is a control device for the electrodes of the electrode set.

It is known that certain cardiac palpitations or arrhythmia phenomena including in particular ventricular and atrial fibrillation but possibly also accelerating tachycardia phenomena which have not yet passed into the state of fibrillation are to be electrotherapeutically treated with good prospects of success by applying short-duration electrical pulses (shocks) to the sensitive cardiac tissue. In order rapidly to achieve termination of such life-threatening arrhythmia effects with a high level of certainty, high energy levels are applied to the cardiac tissue (myocardium), which in many cases results in tissue damage and severe stresses such as pain for the patient. In relation to in particular implantable units, the provision of those high levels of energy requires particularly powerful batteries and capacitors. Those energy storage means are primarily crucial in regard to the structural size of implantable defibrillators. A reduction in the amount of energy required for the shocks permits smaller energy storage means to be used and thus smaller defibrillators. It is known that the energy required can be reduced by an advantageous design configuration in respect of the electrodes and an appropriate actuating mode. U.S. Pat. No. 5,224,476 describes a defibrillator of the general kind set forth, which aims to achieve a reduction in the amount of energy required. That implantable defibrillator has a control device which is arranged in a housing and an electrode set which includes an electrode arranged in the right ventricle, an electrode arranged on the coronary sinus, an electrode arranged in the vena cava, and a patch electrode which is arranged at the apex of the heart or subcutaneously. The control device is designed in such a way that those four electrodes are switched in two pairs and a re successively operated with altering polarities. A disadvantage with this known defibrillator is that it involves an irregular distribution of the electrical field. In addition implantation of the four electrodes of which at least one is a patch electrode which is particularly complicated in terms of implantation is time-consuming and stressful for the patient.

The object of the present invention is that of providing a defibrillator of the kind set forth in the opening part of this specification, which requires less energy for the defibrillation procedure and which is easier to implant.

The way in which that object is attained is set forth in the features of claim 1. Advantageous developments are recited in the appendant claims.

In accordance with the invention, in a defibrillator comprising an implantable housing and an implantable electrode set which includes at least a right-ventricular electrode and a coronary sinus electrode, wherein arranged in the housing is a control device for the electrodes of the electrode set, it is provided that the housing is conductive and is connected as an electrode. The invention is based on the notion that an electrode is formed by the housing of the defibrillator and there is therefore no need now for a patch electrode which is complicated in terms of implantation. The electrode configuration according to the invention provides that an electrical field which is produced upon the output of a shock is more uniformly distributed and is thus effective in a larger region with the same energy used for the field. The energy applied is thus utilised more efficiently. This greater efficiency makes it possible for only a lower level of energy to be sufficient for a shock which is adequate for defibrillation purposes. In practice energy levels of between 4 and 6 joules, preferably about 5 joules, have proven to be adequate to implement defibrillation with sufficient reliability. The defibrillator according to the invention also affords the advantage that it is easier to implant as an electrode is formed by the housing and only two electrodes which are separate from the housing and which are to be inserted directly in the heart are required; in addition there is no longer any need for a patch electrode which is particularly complicated and time-consuming to insert. This means that the implantation operation is easier for the surgeon and causes less stress for the patient. The expression conducting housing is used to mean not only that the housing is formed from an electrically conducting material, but also that the housing comprises a non-conducting material which is provided with a conducting layer.

A defibrillator is admittedly already known in which an electrode is formed by the housing (B. Ken Knight et al 'Dual shock defibrillation with a new lead configuration involving an electrode in the left posterior coronary vein', PACE, Vol 21, April 1998, page 806), but that defibrillator has a different electrode configuration which does not include any coronary sinus electrode but instead a distal electrode which is disposed substantially deeper in the ventricle. Upon shock output that different electrode configuration produces a completely different field configuration which involves a much lower level of efficiency than the field configuration which is afforded by the teaching in accordance with the invention; the consequence of this is that at about 12 joules, a good double the amount of energy is required for the defibrillation procedure, as in the case of the defibrillator according to the invention. In addition the housing electrode in the case of the known defibrillator serves a different purpose from the teaching according to the invention. More specifically, in the case of the known defibrillator, the housing electrode only serves to build up a field for pre-excitation, together with the distal electrode which is disposed deep in the ventricle. The configuration thereof differs from the configuration of the actual shock field which occurs between the other electrodes. The production of that pre-excitation field requires additional energy and is a cause of the high energy requirement of that previously known defibrillator.

Desirably provided as a further electrode is a vena cava electrode which is electrically conductingly connected to the electrode formed by the housing. Particularly uniform distribution of the electrical field is achieved by virtue of this additional electrode which is arranged in the—preferably superior—vena cava and which, by virtue of the conducting connection to the housing, is at the same potential as the housing electrode. Large areas of the myocardium can be affected by the electrical field with the vena cava electrode, while in addition only low levels of leakage losses occur. The latter affords the advantage that unwanted stressing of the ambient tissue by the electrical field does not occur or occurs only to a slight degree.

Desirably, arranged in the housing is a shielding or screening cage which surrounds the control device. The screening cage acts as a Faraday cage and protects the control device from possible negative effects of the electrical fields which are produced upon shock output. The term cage is used to also denote those enclosures which are substantially closed except for individual openings. It will be appreciated that the screening cage comprises a material which is a good conductor. Advantageously, the screening cage is also such as to afford shielding from magnetic fields.

In accordance with a particularly advantageous embodiment the control device is connected in such a way that it operates the electrodes with a shock which has at least three phases and at least one change in polarity, with the electrode being actuated in all phases. The term change in polarity is used to mean that the electrode (or electrodes) which are connected as a cathode in one phase are connected as an anode in a following phase, and vice-versa. The fact that an electrode is actuated in all phases means that there are no completely separated field configurations in respect of the electrical field, because of the common electrode, as viewed over all phases. As the field patterns partially overlap, there is an implicit pre-excitation effect in the regions which are in the field configuration of a plurality of phases. This permits a further reduction in the amount of energy required to implement defibrillation.

Preferably the control device is switched in such a way that in a first phase a first electrode of the electrode set and a second electrode of the electrode set are actuated, in a subsequent phase the first electrode and a third electrode of the electrode set are actuated and in a further subsequent phase the first electrode and the second or third electrode are actuated with the reverse polarity. A three-phase mode of actuation of that nature, together with the electrode configuration according to the invention, has the advantage of affording a uniform distribution of the electrical field upon shock output, such as to avoid local peaks. It is particularly preferred if the right-ventricular electrode is the first electrode, the coronary sinus electrode is the second electrode and the housing is the third electrode. That affords in the first phase a concentration of the field and therewith the field energy in the ventricle region of the heart. That has the advantage that losses due to a field pattern outside the ventricle can be substantially avoided. A further advantage is that the ventricle is already depolarised thereby in the first phase. As the housing acts as an electrode which is extended in terms of surface area, the arrangement affords a uniform field distribution which is advantageous for acting on the entire ventricle. It has surprisingly been found that, in spite of the large field-filled space which is governed by the arrangement, remote from the heart, of the counterpart electrode in the form of the housing, only a lower level of energy is required than if—as in the known defibrillator—the more closely disposed vena cava electrode is the counterpart electrode.

Desirably the control device is switched in such a way that it actuates the electrodes with a shock which involves five phases. That can provide an even more uniform distribution of the electrical field over the myocardium. Preferably the five-phase shock, originating from the three-phase shock, is formed in such a way that phases one and two are the first two phases of the three-phase shock, phases three and four are a repetition of the first two, and the phase five corresponds to the third phase of the three-phase shock. It can also be provided that repetition of the first two phases includes a change in polarity. The five-phase shock has the advantage, in particular in conjunction with the electrode arrangement according to the invention, that the even more uniform distribution of the electrical field further minimises the losses and/or the stressing of the surrounding tissue by the electrical field.

Frequently, the control device is switched in such a way that the phases of a shock are of the same or at least an approximately identical time duration. The control device however can also be switched in such a way that the time durations of the various phases are different. Preferably then the duration of the first phase which is frequently also referred to as the phase zero is less than that of the following phase.

In an advantageous embodiment of the present invention the control device is so switched for the output of an atrial shock that it actuates the coronary sinus electrode and the vena cava electrode. In that way both atrial flutter and also atrial fibrillation can be specifically terminated by the output of an atrial shock, more specifically in such a way that the electrical field which is produced upon output of the shock is concentrated on the atria. The concentration effect both reduces the amount of energy required for the shock and also avoids unnecessarily stressing the rest of the cardiac tissue by the electrical field, or at least at any event alleviates it.

Preferably in that respect the control device is switched in such a way that it actuates the housing electrode together with the vena cava electrode. The fact that the vena cava electrode and the housing electrode are then at a common potential provides for uniform involvement of both atria with the electrical field which is produced upon output of the shock.

Figure 2:
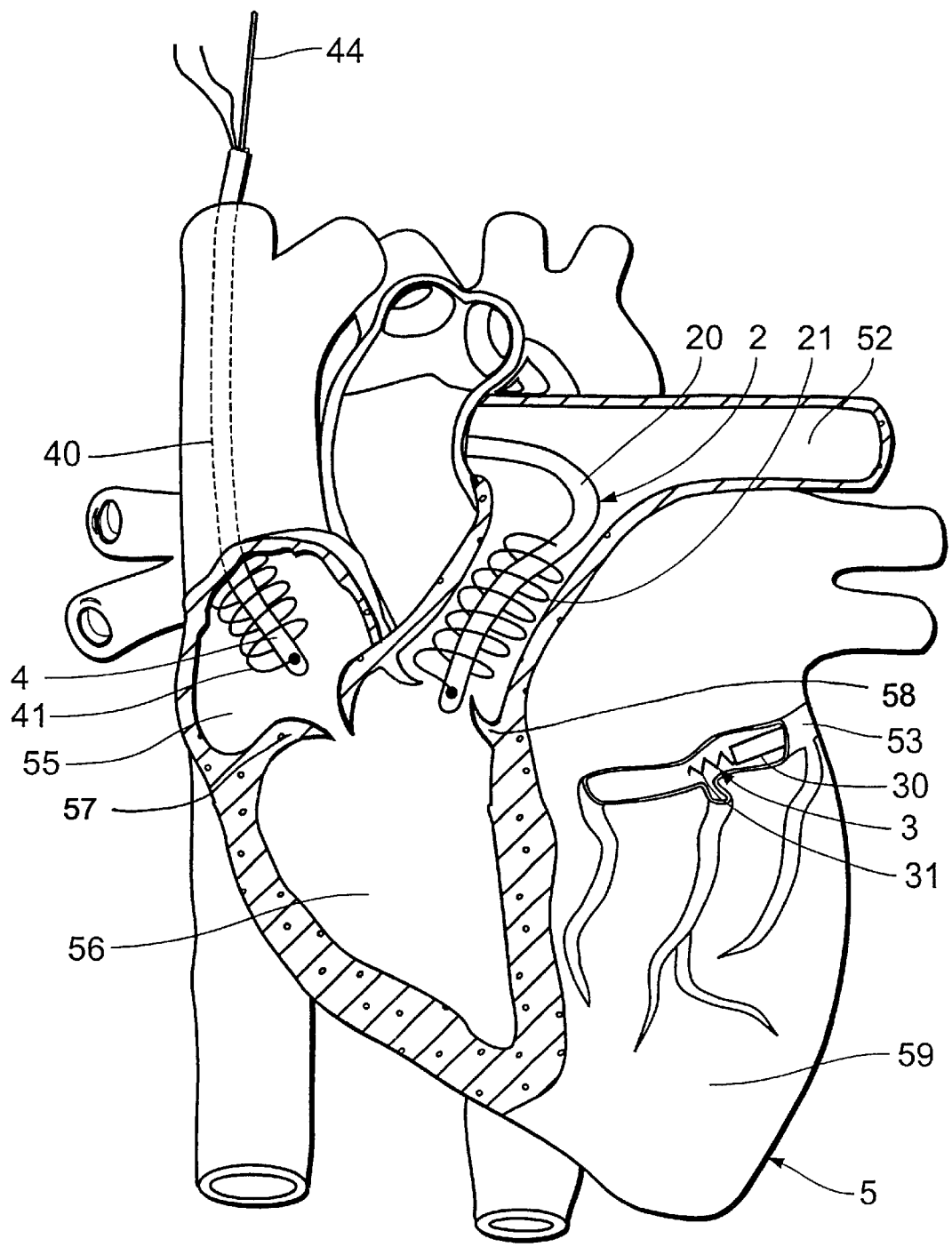
Figure 3:
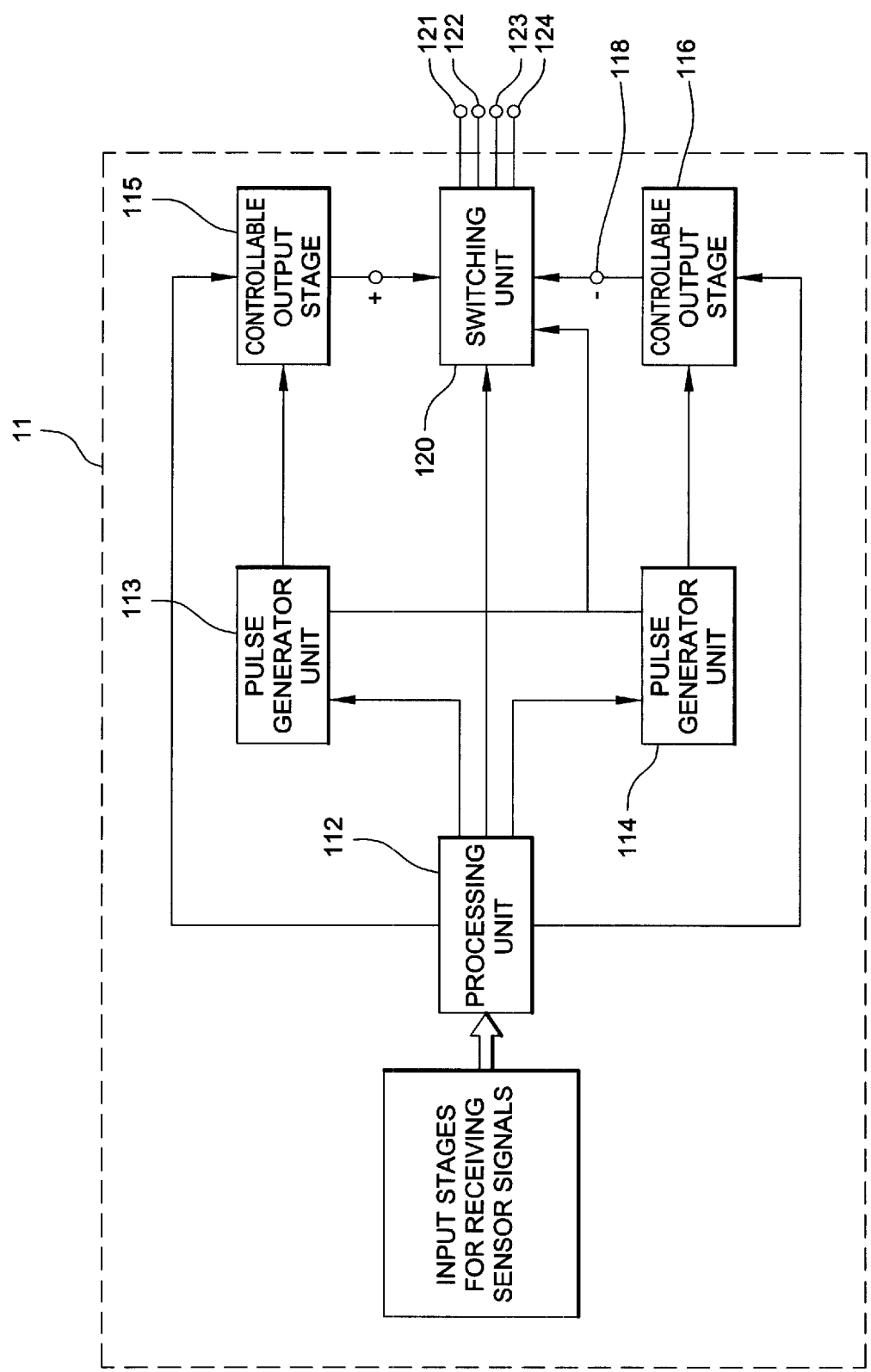

The invention is described in greater detail hereinafter by means of an embodiment with reference to the accompanying drawings in which:

FIG. 1 shows a defibrillator according to the invention with electrodes inserted into the heart, FIG. 2 is a view on an enlarged scale of the electrodes inserted into the heart, and FIG. 3 is a diagrammatic view of a control device of the defibrillator according to the invention.

Referring to FIG. 1, shown therein is a defibrillator 1 comprising an electrode set in accordance with the present invention. Arranged in a housing 10 of the defibrillator 1 is a screening cage 12 and therein a control device 11. The control device 11 is connected by way of an electrode line 13 to electrodes 2, 3, 4 of the electrode set, which are arranged in a heart 5. The spatial arrangement of the heart 5, the housing 1 and the electrode line 13, as shown in FIG. 1, is diagrammatic and does not need to correspond to the anatomical conditions involved.

The electrode set includes the housing 10 of the defibrillator 1, a right-ventricular electrode 2, a coronary sinus electrode 3 and a vena cava electrode 4. The control device 11 is electrically conductively connected by way of branches 22, 33 and 44 of the electrode line 13 to the right-ventricular electrode 2, the coronary sinus electrode 3 and the vena cava electrode 4 respectively. The control device 11 is electrically conductingly connected to the housing 10 by way of a further branch (not shown) of the electrode line 13.

The housing 10 comprises a biocompatible material which is a good conductor. The screening cage 12 comprises a material which affords a high level of conductivity for shielding electrical fields and preferably also permeability for shielding magnetic fields.

A heart 5 with, inserted therein, a right-ventricular electrode 2, a coronary sinus electrode 3 and a vena cava electrode 4 is shown in FIG. 2. Shown on the left-hand side in FIG. 2 is right atrium 55, a right ventricle 56, a tricuspid flap 57 arranged therebetween, and a pulmonary flap 58 between the right ventricle 56 and a pulmonary artery 52. Shown on the right-hand side in FIG. 2 is a left ventricle 59 and a coronary sinus 53.

The right-ventricular electrode 2 is inserted in the region of the right ventricle 56 of the heart 5. In the view shown in FIGS. 1 and 2 the right-ventricular electrode 2 is inserted at the pulmonary side from the pulmonary flap 58. The possibility of the right-ventricular electrode 2 being inserted further advanced within the right ventricle 56 should however not be excluded. In this case it may be desirable for the branch 22 of the electrode line 13, which leads to the right-ventricular electrode 2, to be passed not through the pulmonary flap 58 but by way of the right atrium 55 through the tricuspid flap 57. The right-ventricular electrode 2 has an electrode body 20 and arranged at its distal end an electrically conductive coil 21 as a shock coil. The coil 21 is electrically conductingly connected to the branch 22 of the electrode line 13, which leads to the right-ventricular electrode 2.

The coronary sinus electrode 3 is inserted posteriorly between the left atrium and the left ventricle 59 in a distal region of the coronary sinus 53. For the sake of enhanced clarity of the drawing the coronary sinus 53 is shown in partly cut-open form in FIGS. 1 and 2. The coronary sinus electrode 3 has an electrode body 30 and, arranged at its distal end, a coil 31 as the shock coil. Alternatively, instead of the coil 31, it is also possible to provide other elements such as points (not shown). The coil 31 is electrically conductingly connected to the branch 33 of the electrode line 13.

The vena cava electrode 4 is arranged in a hollow vein, more precisely in the superior vena cava. It has an electrode body 40 and, arranged at its distal end, an electrically conducting coil 41 as a shock coil. The coil 41 is electrically conductingly connected to the branch 44 of the electrode line 13, which leads to the vena cava electrode 4.

In order to permit easier insertion of the electrodes 2, 3 and 4 disposed in the heart, one or more of the branches 22, 33, 44 of the electrode line 13 have in their distal region near the electrodes 2, 3, 4 memory metal structures which preferably contain titanium. This affords the advantage that, prior to the implantation procedure, the branches 22, 33, 44 of the electrode line 14 can be of a first shape which is advantageous for the insertion operation and, after the electrodes 2, 3, 4 have been inserted, they can be put by heating into a predetermined second shape which is adapted to the respective anatomical factors of the place of insertion.

The control device 11 which is arranged in the housing 10 is shown in greater detail in FIG. 3. Arranged on the side at the left in FIG. 3 are connections and input stages for receiving sensor signals. That is known from the state of the art and is therefore not described in further detail hereinafter. A processing unit 112 is connected to the input stages. The processing unit 112 implements in a manner which is known per se and which is not of further interest here an analysis operation in respect of the signals originating from the input stages and in accordance with a result of the analysis operation actuates first and second pulse generator units 113, 114; for that purpose, it is connected to a respective input of each of the pulse generator units 113, 114. An input of a first controllable output stage 115 is connected to an output of the first pulse generator unit 113 and an input of a second controllable output stage 116 is connected to an output of the second pulse generator unit 114, in such a way that a first voltage pulse of predetermined amplitude of positive polarity is produced at a first defibrillator output 117 and a second voltage pulse of predetermined amplitude of negative polarity is produced at a second defibrillator output 118, in each case in relation to the circuit ground as the reference point. The processing unit 112 is also connected by way of a control output to an input of a switching unit 120. Further inputs of the switching unit 120 are connected to the outputs 117, 118 while outputs of the switching unit are connected to electrode connections 121, 122, 123 and 124. The electrode connections 122, 123, 124 are connected by way of the branches 22, 33, 44 of the electrode line 13 to respective ones of the electrodes 2, 3 and 4 respectively while the electrode connection 121 is connected to the housing 10 which is thus connected as a housing electrode.

In accordance with a switching scheme which is stored in the switching unit 120 and which is selected from a plurality of stored switching schemes using the control signal, the inputs of the switching unit 120 are connected by way of the electrode connections 121, 122, 123 and 124 to selected ones of the electrodes 10, 2, 3, 4. By virtue of that selection of electrodes, a shock pulse field of an intensity which is above the defibrillation threshold is produced in a predetermined region of the heart 5, more precisely in a predetermined region of the myocardium, in which case at the same time an undesirable influence on the remaining tissue of the heart 5 and/or surrounding tissue (not shown) is minimised.

More precisely, a shock involving the following phases is outputted for defibrillation purposes: in a phase zero the right-ventricular electrode 2 is connected as a cathode and the coronary sinus electrode 3 is connected as an anode, by the switching unit 120; in a phase one the right-ventricular electrode 2 is connected as a cathode and the housing electrode 10 and the vena cava electrode 4 are connected as an anode; and in a phase two the housing electrode 10 and the vena cava electrode 4 are connected as a cathode and the right-ventricular electrode 2 is connected as an anode. That means that phase two corresponds to phase one with the reversed polarity.

With this embodiment of the invention it was possible to achieve a reduction in the amount of energy required for defibrillation purposes to about 5 joules.

A second embodiment provides that a shock for defibrillation purposes has five phases: in phases zero and one the electrodes are switched in a fashion corresponding to the phases zero and one of the free-phase shock mode; phases two and three are a repetition of the phases zero and one; and in phase four the electrodes are connected in a manner corresponding to phase two of the three-phase shock mode. The five-phase shock mode differs from the three-phase shock mode therefore essentially in that the phases zero and one are repeated once. This means that the procedure switches over a plurality of times between the coronary sinus electrode 3 on the one hand and the housing electrode 10 with the vena cava electrode 4 on the other hand as the anode. That provides for even more uniform and regular distribution of the field produced upon shock output, across the right and left ventricles.

The specified phases in the shocks are minimum phases; it will be appreciated that they may have further phases and/or changes in polarity.

What is claimed is:

1. A defibrillator comprising:
   an implantable electrode set which includes at least a right-ventricular electrode and a coronary sinus electrode; and
   an implantable housing, the implantable housing having therein a control device for the electrodes of the implantable electrode set, and the implantable housing being conducting and connected as a housing electrode;
   wherein the control device actuates:
   in a first phase, the right-ventricular electrode and the corornary sinus electrode;
   in a second phase following the first phase, the right-ventricular electrode and the housing electrode; and
   in a third phase following the second phase, the right-ventricular electrode and one of the coronary sinus electrode and the housing electrode with reversed polarity.

2. A defibrillator as set forth in claim 1 further comprising a vena cava electrode which is electrically conductingly connected to the housing electrode such that the control device actuates the coronary sinus electrode and the vena cava electrode for outputting an atrial shock.

3. The defibrillator as set forth in claim 1 wherein arranged in the implantable housing is a screening cage surrounding the control device.

4. The defibrillator as set forth in claim 1, wherein the control device is so switched that the first phase has a time duration that is the same as or less than that of the second phase.

5. A defibrillator comprising:

an implantable electrode set which includes at least a right-ventricular electrode and a coronary sinus electrode; and an implantable housing, the implantable housing having therein a control device for the electrodes of the implantable electrode set, and the implantable housing being conducting and connected as a housing electrode;

wherein the control device actuates:

in a first phase, the right-ventricular electrode and the corornary sinus electrode;

in a second phase following the first phase, the right-ventricular electrode and the housing electrode;

in a third phase following the second phase, the right-ventricular electrode and the coronary sinus electrode;

in a fourth phase following the third phase, the right-ventricular electrode and the housing electrode; and in a fifth phase following the fourth phase, the right-ventricular electrode and one of the coronary sinus electrode and the housing electrode with reversed polarity.

6. The defibrillator as set forth in claim 5, further comprising a vena cava electrode which is electrically conductingly connected to the housing electrode such that the control device actuates the coronary sinus electrode and the vena cava electrode for outputting an atrial shock.

7. The defibrillator as set forth in claim 5, wherein arranged in the implantable housing is a screening cage surrounding the control device.

8. The defibrillator as set forth in claim 5, wherein the control device is so switched that the first phase has a time duration that is either the same as or is less than that of the second phase.

* * * * *